(12) United States Patent
Ewers et al.

(10) Patent No.: US 9,572,565 B2
(45) Date of Patent: Feb. 21, 2017

(54) LOW PROFILE TISSUE ANCHORS, TISSUE ANCHOR SYSTEMS, AND METHODS FOR THEIR DELIVERY AND USE

(71) Applicant: USGI MEDICAL, INC., San Clemente, CA (US)

(72) Inventors: Richard C. Ewers, San Clemente, CA (US); Tracy D. Maahs, San Clemente, CA (US); Shirley Vong, San Clemente, CA (US)

(73) Assignee: USGI Medical, Inc., San Clemente, CA (US)

( * ) Notice: Subject to any disclaimer, the term of this patent is extended or adjusted under 35 U.S.C. 154(b) by 204 days.

(21) Appl. No.: 14/503,641

(22) Filed: Oct. 1, 2014

(65) Prior Publication Data

US 2015/0018876 A1 Jan. 15, 2015

Related U.S. Application Data

(63) Continuation of application No. 11/773,933, filed on Jul. 5, 2007, now Pat. No. 8,870,916.

(60) Provisional application No. 60/819,054, filed on Jul. 7, 2006.

(51) Int. Cl.
*A61B 17/04* (2006.01)
*A61B 17/06* (2006.01)
*A61B 17/22* (2006.01)
*A61B 17/28* (2006.01)
(Continued)

(52) U.S. Cl.
CPC ....... *A61B 17/0401* (2013.01); *A61B 17/0487* (2013.01); *A61B 17/06166* (2013.01); *A61B 17/22031* (2013.01); *A61B 17/282* (2013.01); *A61B 17/29* (2013.01); *A61B 2017/00004* (2013.01); *A61B 2017/00526* (2013.01); *A61B 2017/00862* (2013.01); *A61B 2017/00986* (2013.01); *A61B 2017/0403* (2013.01); *A61B 2017/048* (2013.01); *A61B 2017/0409* (2013.01); *A61B 2017/0417* (2013.01); *A61B 2017/0451* (2013.01); *A61B 2017/0458* (2013.01); *A61B 2017/0496* (2013.01); *A61B 2017/061* (2013.01)

(58) Field of Classification Search
CPC ............ A61B 17/0401; A61B 17/0487; A61B 17/22031; A61B 17/282; A61B 17/29; A61B 2017/00004; A61B 2017/00526; A61B 2017/00862; A61B 2017/0403; A61B 2017/0409; A61B 2017/0417; A61B 2017/0451; A61B 2017/0458; A61B 2017/04
See application file for complete search history.

(56) References Cited

U.S. PATENT DOCUMENTS

| 5,350,399 A | 9/1994 | Erlebacher et al. |
| 5,709,707 A | 1/1998 | Lock et al. |
| 6,068,648 A | 5/2000 | Cole et al. |

(Continued)

*Primary Examiner* — Julian W Woo
(74) *Attorney, Agent, or Firm* — Kenneth H. Ohriner; Perkins Coie LLP

(57) ABSTRACT

Tissue anchors include a flat, broad, and large contact surface for engagement with a portion of tissue. Several embodiments of composite tissue anchors include a support element and an overlay element. Tissue anchor assemblies include two or more tissue anchors, a connector, and a cinching mechanism. In some embodiments, the tissue anchors included in the tissue anchor assemblies are of different types, sizes, and/or shapes.

19 Claims, 17 Drawing Sheets

(51) Int. Cl.
 *A61B 17/29* (2006.01)
 *A61B 17/00* (2006.01)

(56) References Cited

U.S. PATENT DOCUMENTS

| | | |
|---|---|---|
| 7,621,925 B2 | 11/2009 | Saadat |
| 7,678,135 B2 | 3/2010 | Maahs et al. |
| 7,736,379 B2 | 6/2010 | Ewers et al. |
| 8,066,719 B2 | 11/2011 | Ewers et al. |
| 8,083,768 B2 * | 12/2011 | Ginn .................. A61B 17/0057 424/422 |
| 8,216,260 B2 | 7/2012 | Lam et al. |
| 8,262,676 B2 | 9/2012 | Ewers et al. |
| 8,382,800 B2 | 2/2013 | Maahs et al. |
| 8,740,940 B2 | 6/2014 | Maahs et al. |
| 2005/0273135 A1 | 12/2005 | Chanduszko |
| 2007/0112382 A1 * | 5/2007 | Thill .................. A61B 17/0057 606/213 |

* cited by examiner

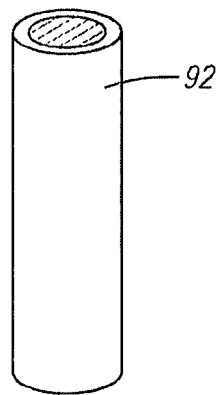 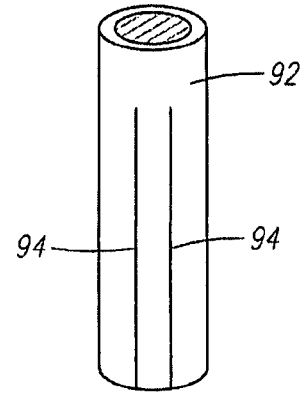
*FIG. 3A*  *FIG. 3B*
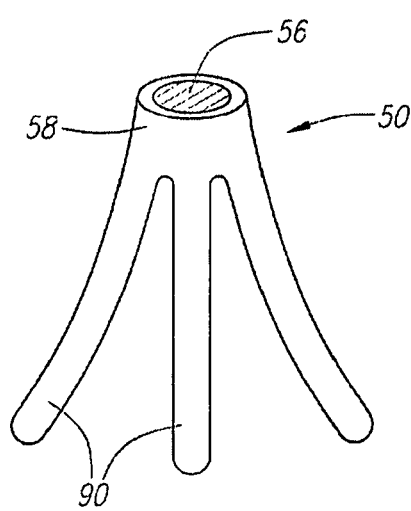 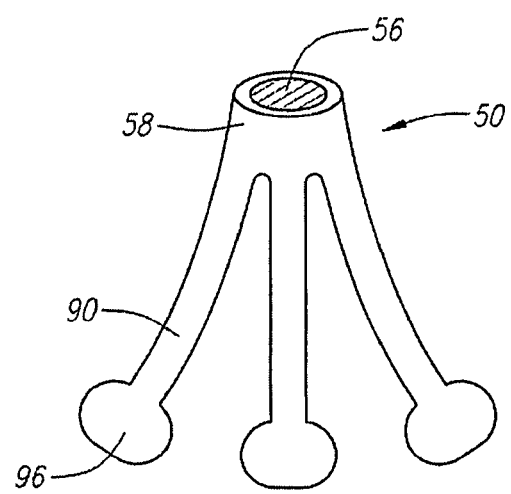
*FIG. 3C*  *FIG. 3D*

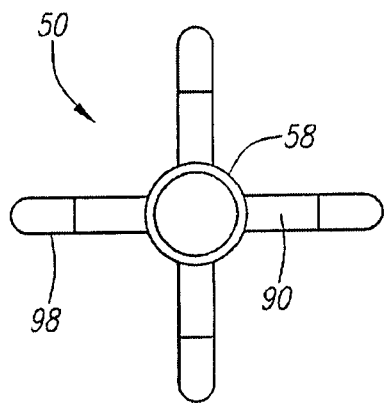 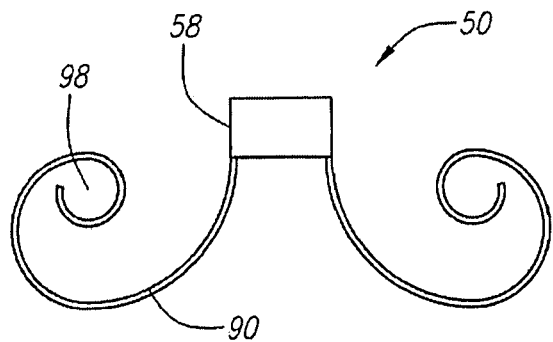
FIG. 4A  FIG. 4B
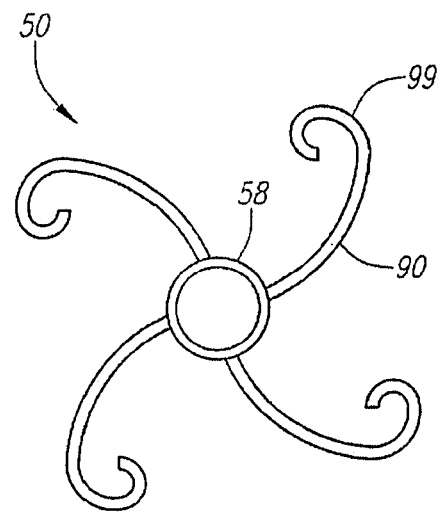 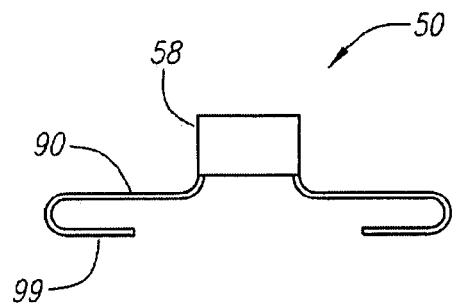
FIG. 5A  FIG. 5B

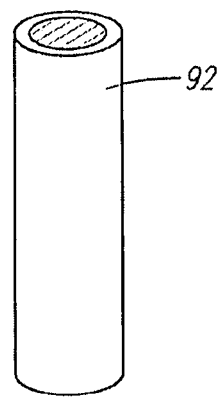
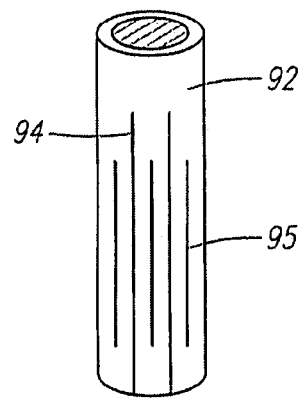
FIG. 6A         FIG. 6B
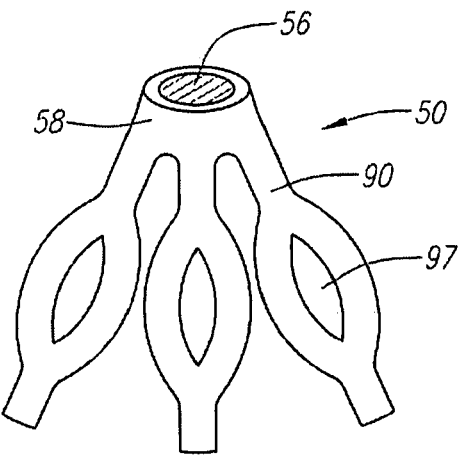
FIG. 6C
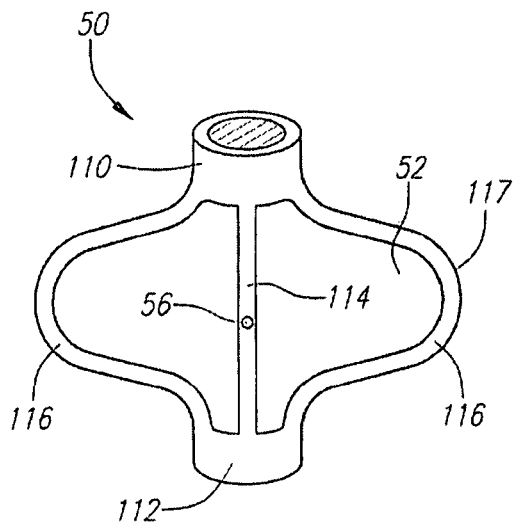
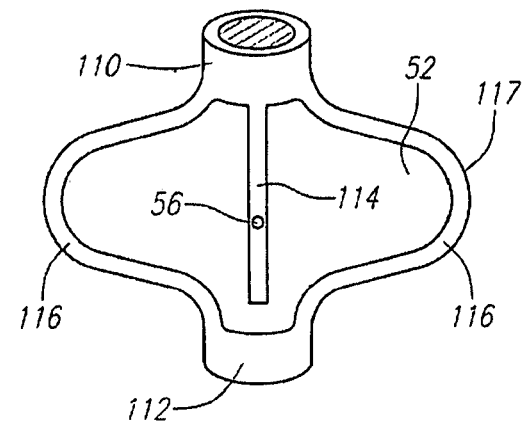
FIG. 7A         FIG. 7B

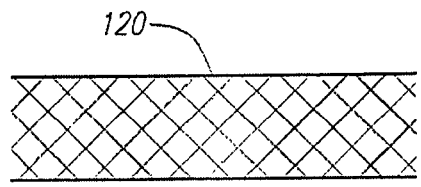 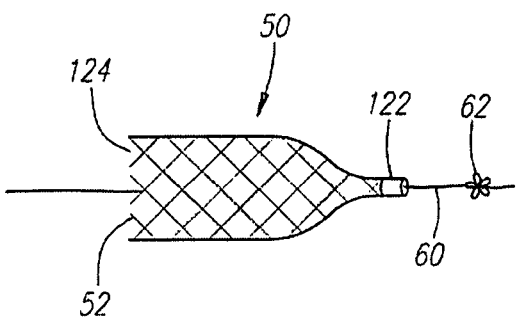
FIG. 8A  FIG. 8B
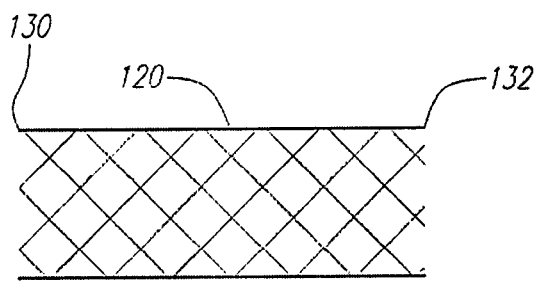 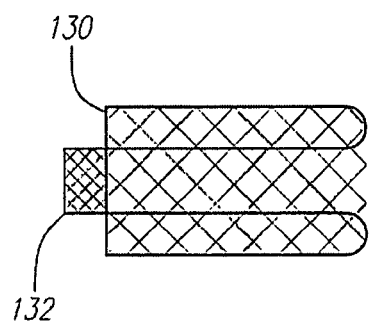
FIG. 9A  FIG. 9B
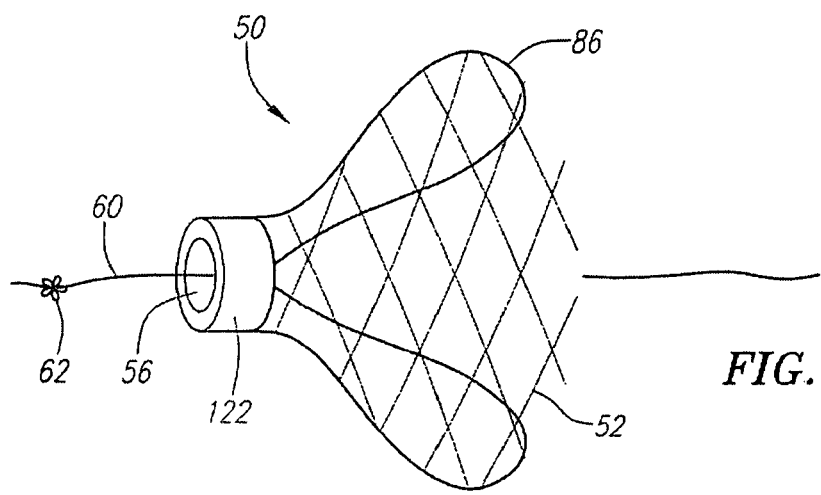
FIG. 9C

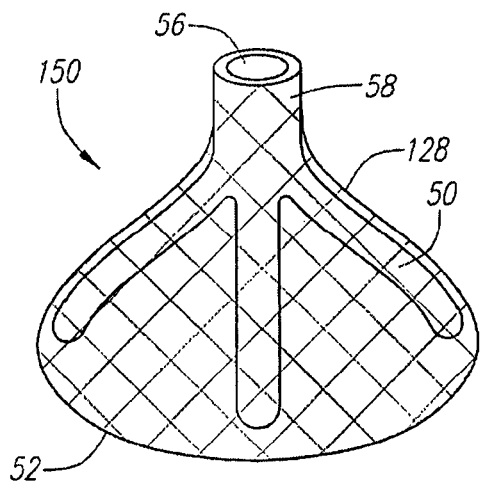
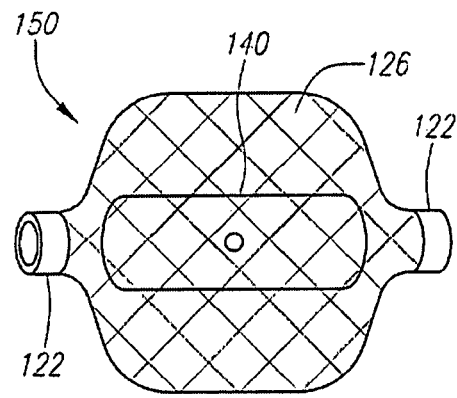
FIG. 13    FIG. 14
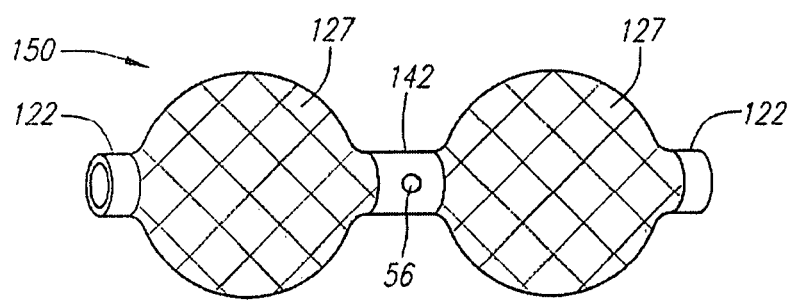
FIG. 15A
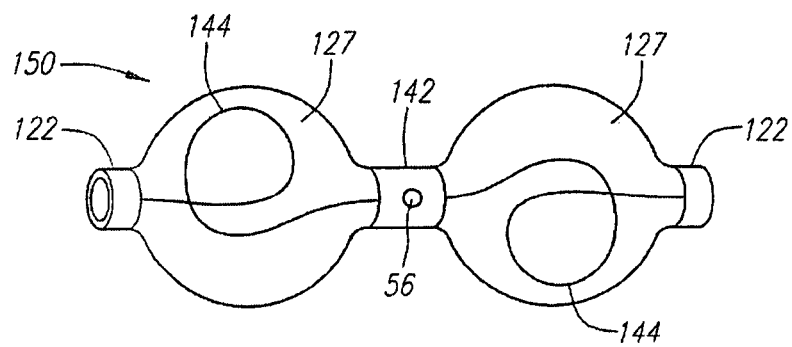
FIG. 15B

LOW PROFILE TISSUE ANCHORS, TISSUE ANCHOR SYSTEMS, AND METHODS FOR THEIR DELIVERY AND USE

PRIORITY CLAIM

This application is a Continuation of U.S. patent application Ser. No. 11/773,933 filed Jul. 5, 2007, and now pending, which claims priority to U.S. Provisional Patent Application No. 60/819,054, filed Jul. 7, 2006. All applications are incorporated herein by reference in their entirety.

FIELD OF THE INVENTION

The present invention relates to methods and apparatus for deploying tissue anchors into or against one or more tissue regions and to tissue anchors that are deployable from a low-profile configuration to an expanded configuration.

BACKGROUND OF THE INVENTION

Many surgical and other therapeutic or diagnostic procedures include steps of reconfiguring, fixing, or otherwise manipulating tissue in some manner, or joining two or more portions of tissue together. Several devices have been used to perform these functions, including sutures, staples, screws, anchors, clips, tags, and other similar types of devices.

Many of the conventional sutures, staples, clips, tags, and anchors that are used in these procedures require extensive training by the clinician to achieve competent use. In addition, many of the devices concentrate significant force over a small surface area of the tissue, thereby potentially causing the suture, staple, or anchor to tear through the tissue.

Many of the procedures require regions of tissue within the body to be approximated towards one another and reliably secured. For example, several surgical procedures are performed in which tissue in the gastrointestinal lumen is approximated, such as gastric reduction. The gastrointestinal lumen includes four tissue layers, wherein the mucosa layer is the inner-most tissue layer followed by connective tissue, the muscularis layer and the serosa layer. One problem with conventional gastric reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intraoperatively, since care must be taken in piercing the tough stomach wall not to inadvertently puncture adjacent tissue or organs.

One conventional method for securing anchors within a body lumen to the tissue is to utilize sewing devices to suture the stomach wall into folds. This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity, GERD, or other procedures must be performed to completion. Accordingly, the placement and securement of the tissue plication should ideally be relatively quick and performed with a high level of confidence.

Another problem with conventional securement methods is ensuring that the staple, knotted suture, tag, anchor, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally, transrectally, or transvaginally.

Moreover, when grasping or clamping onto or upon the layers of tissue with conventional anchors, sutures, staples, clips, etc., may of these devices are configured to be placed only after the tissue has been plicated and not during the actual plication procedure.

SUMMARY

In a first aspect, a tissue anchor includes a flat, broad contact surface on a first side and an exposed surface on an opposite side. The flat, broad contact surface allows the tissue anchor to rest substantially flat against the surface of the tissue so that the force imparted by the anchor is substantially evenly distributed over the engagement surface. This feature is believed to facilitate and promote tissue healing and reconfiguration. This feature is also believed to increase the holding strength of the tissue anchor system, and increased the resistance to pull-through of the anchor (i.e., the tendency of an anchor to be pulled through a hole or other defect in the tissue under the tension force from the connector). Moreover, the absence of a collar or other component projecting from the contact surface of several of the tissue anchor embodiments described below allows the tissue anchor assemblies incorporating those anchors to more closely approximate portions of tissue, or to approximate portions of thin tissue more effectively than would otherwise be possible with conventional tissue anchor systems.

In several embodiments, the tissue anchor includes a woven material that makes up all or a portion of the contact surface. In some embodiments, the woven material is a mesh or braid formed of a biocompatible and/or bioabsorbable material. In some embodiments, the entire tissue anchor is formed of the woven material. In other embodiments, the tissue anchor includes an overlay of a woven material, such as a woven pouch, that is supported by an underlying support structure, such as a support bar, a support ring, and/or a strutted anchor structure. In still other embodiments, a sheet or plurality of sheets of woven material are supported by a frame formed of a resilient material.

In another aspect, a tissue anchor assembly includes at least one distal anchor, at least one proximal anchor, a connector extending between and interconnecting the distal and proximal anchors, and a retainer mechanism that retains the distal and proximal anchors at a substantially maximum distance from each other on the connector when the tissue anchor assembly is deployed through tissue. In some embodiments, the distal anchor and proximal anchor of the tissue anchor assembly are of the same or similar construction. In other embodiments, the distal anchor and proximal anchor are of different constructions. For example, in an embodiment, the distal anchor is a basket-type anchor having a first collar, a second collar, and a collapsible basket structure interposed between the two collars, while the proximal anchor is a flat, composite tissue anchor having a woven pouch containing a support bar and a support ring. In another embodiment, both the proximal and distal anchors are of the composite tissue anchor type described above. These embodiments are exemplary, and are not intended to be limiting. All other combinations that include one or more of the tissue anchors described herein are also contemplated.

In another aspect, a delivery device for reconfiguring tissue and delivering a tissue anchor assembly includes a tissue manipulation assembly and a needle deployment assembly. The tissue manipulation assembly includes a flexible shaft and a tissue manipulation end effector adapted to grasp and manipulate tissue. The needle deployment assembly includes a flexible shaft having a hollow needle at its distal end. The needle deployment assembly is adapted to extend through the tissue manipulation assembly shaft, with the hollow needle extending through a portion of tissue held by the tissue manipulation end effector. A tissue anchor or tissue anchor assembly is releasably received in the hollow needle, and is deployed out of the needle deployment assembly under control of the user.

BRIEF DESCRIPTIONS OF THE DRAWINGS

FIGS. 1A-C are side views of three embodiments of tissue anchors.

FIGS. 2A-B are side views of a tissue anchor assembly in a transition state and a deployed state, respectively.

FIGS. 3A-D are side views of a tube and of embodiments of a tissue anchor, illustrating a method of making the tissue anchors.

FIGS. 4A-B are a top view and a side view, respectively, of a tissue anchor.

FIGS. 5A-B are a top view and a side view, respectively, of a tissue anchor.

FIGS. 6A-C are side views of a tube and of an embodiment of a tissue anchor, illustrating a method of making the tissue anchors.

FIGS. 7A-B are side views of two embodiments of a tissue anchor.

FIGS. 8A-B are side views of a mesh sleeve and an open-ended mesh tissue anchor formed from the mesh sleeve, respectively.

FIGS. 9A-C are side views of a mesh sleeve, an inverted mesh sleeve, and a mesh tissue anchor having a non-fraying transition formed from the mesh sleeve, respectively.

FIGS. 10A-B are side views of a mesh sleeve and a mesh pouch formed from the mesh sleeve, respectively.

FIG. 13 is a side view of a composite tissue anchor including a strutted anchor and a mesh anchor overlaying the strutted anchor.

FIG. 14 is a side view of a composite tissue anchor including a T-bar retained within a mesh pouch.

FIGS. 15A-B are side views of a composite tissue anchor including a center collar and a pair of support coils on a mesh pouch.

Figure 16:
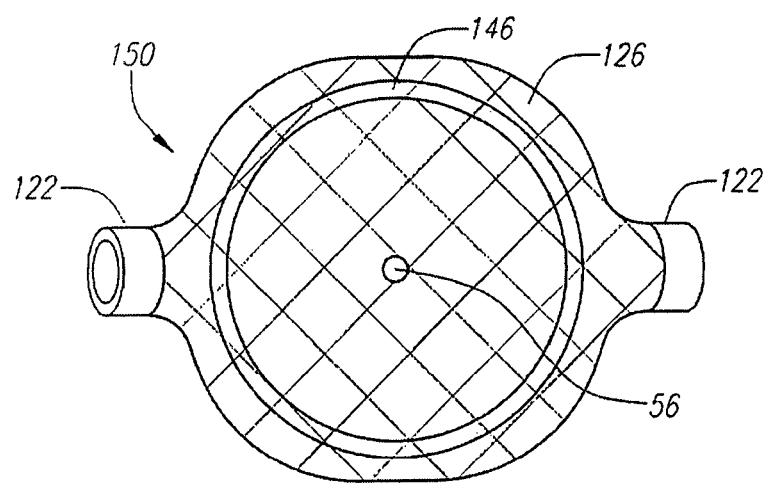

FIG. 16 is a side view of a composite tissue anchor including a support ring retained within a mesh pouch.

Figure 17:
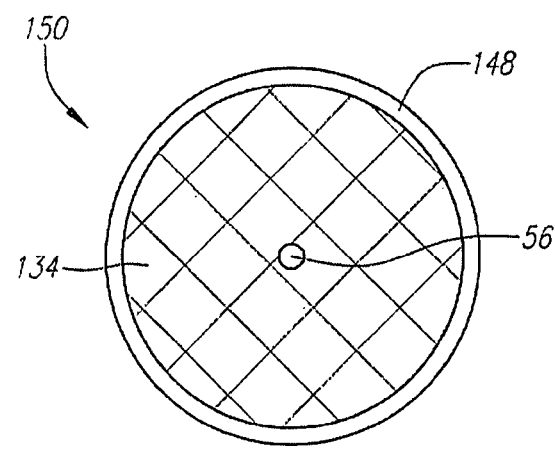

FIG. 17 is a side view of a composite tissue anchor including a mesh sheet attached to a frame.

Figure 18A:
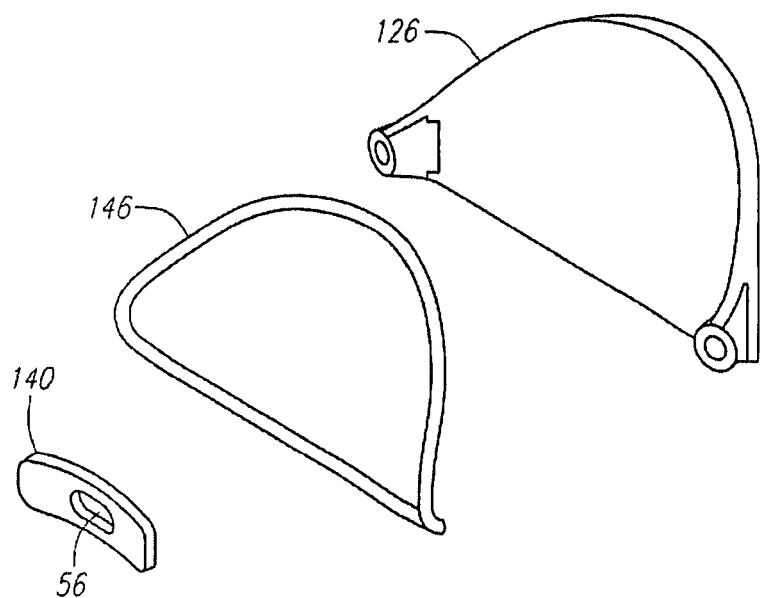
Figure 18B:
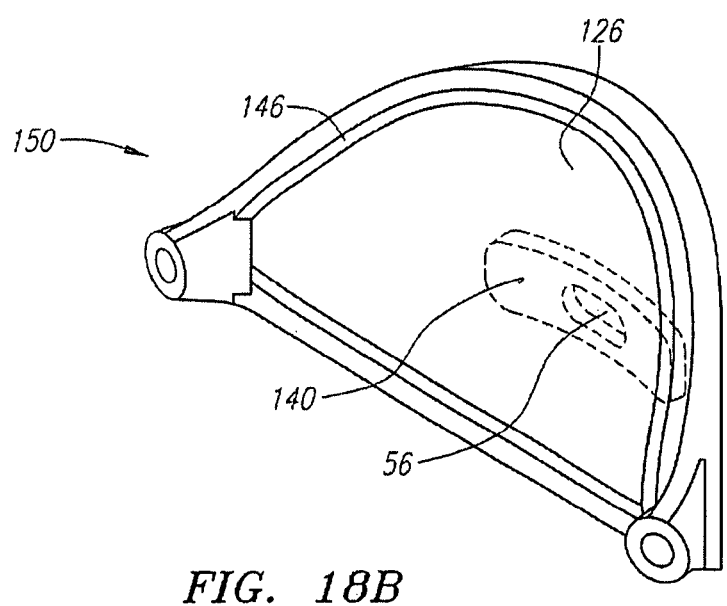

FIGS. 18A-B are an exploded view and a perspective view of a composite tissue anchor including a support ring and a cross-bar retained within a mesh pouch.

Figure 19A:
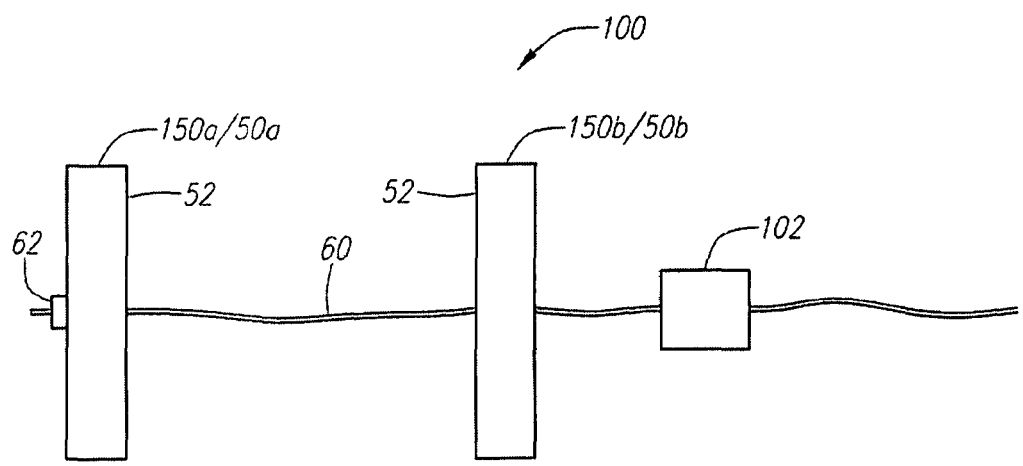
Figure 19B:
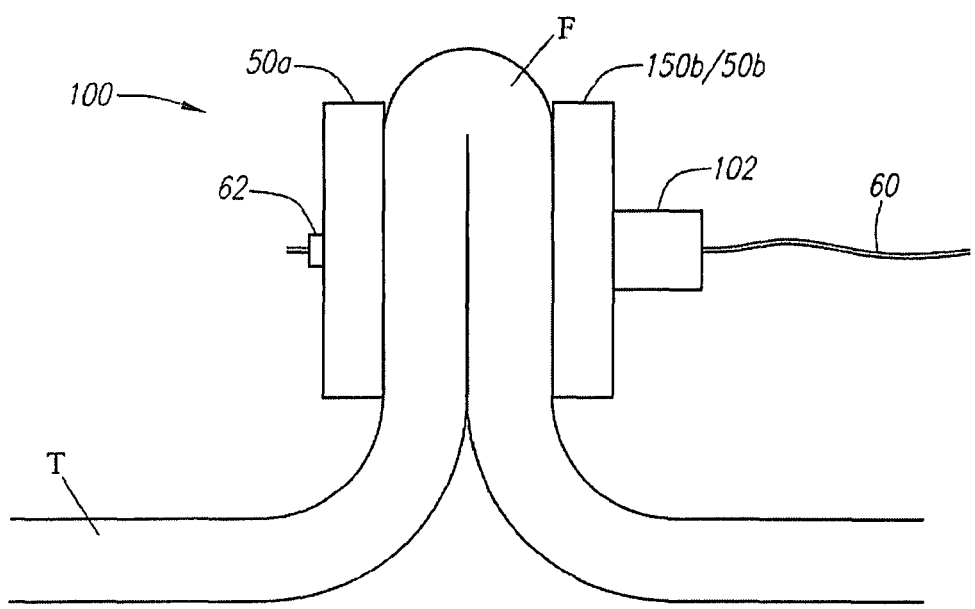

FIGS. 19A-B are side schematic views illustrating a method for approximating a tissue fold using a tissue anchor assembly.

Figure 20A:
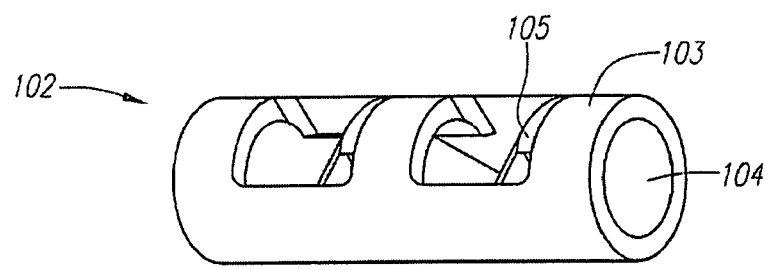
Figure 20B:
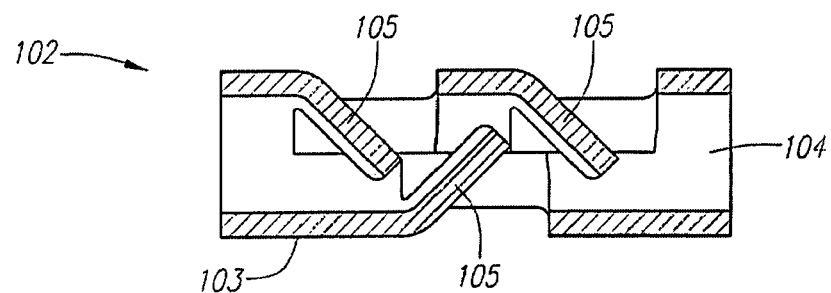

FIGS. 20A-B are perspective and cross-sectional views, respectively, of a cinch.

Figure 21:
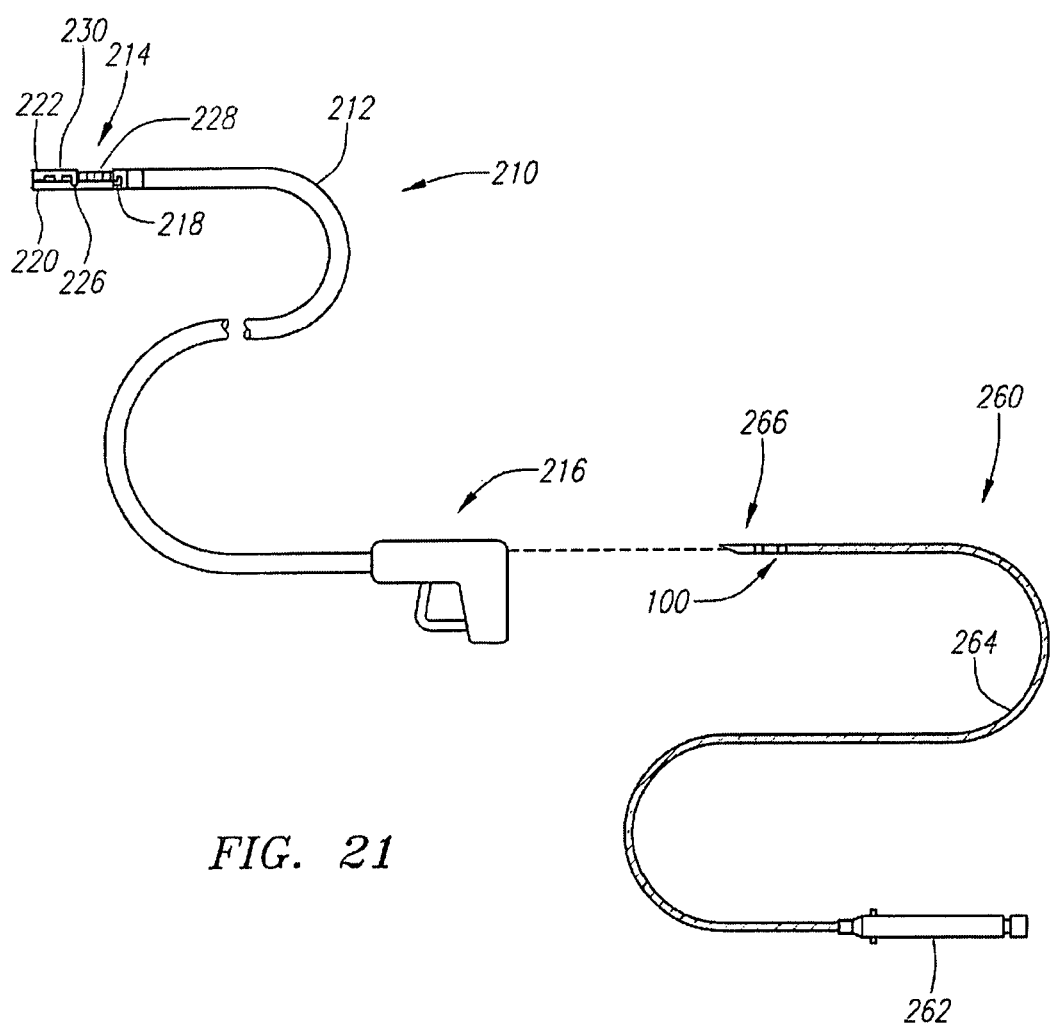

FIG. 21 is an assembly view showing how a needle deployment assembly is introduced through a handle and tubular body of a tissue manipulation assembly.

Figure 22:
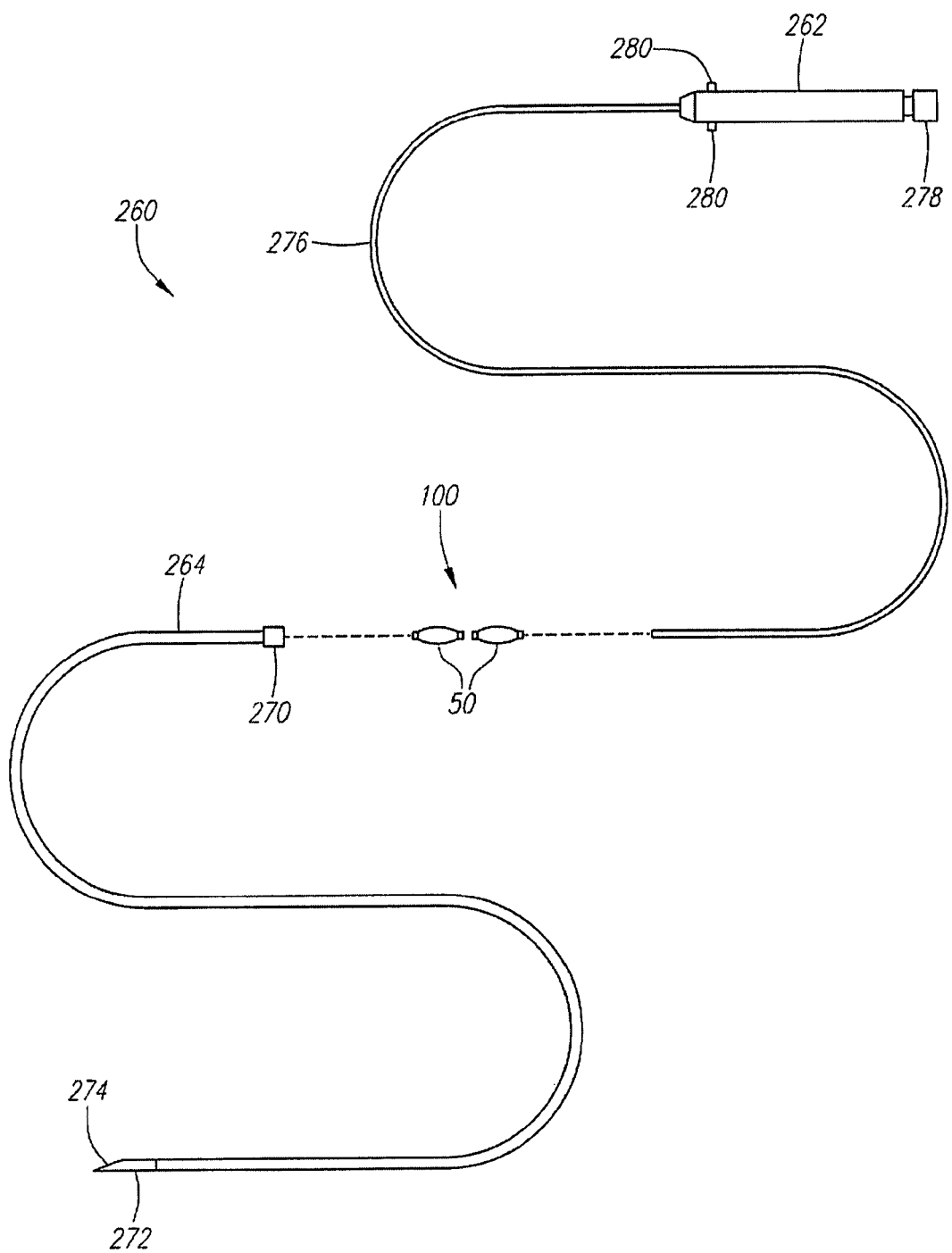

FIG. 22 is an exploded assembly view of the needle deployment assembly from FIG. 21.

Figure 23A:
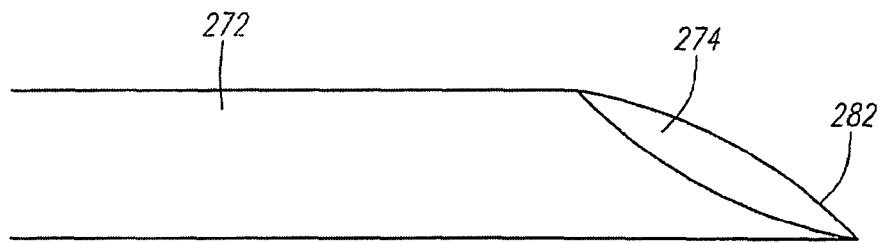
Figure 23B:
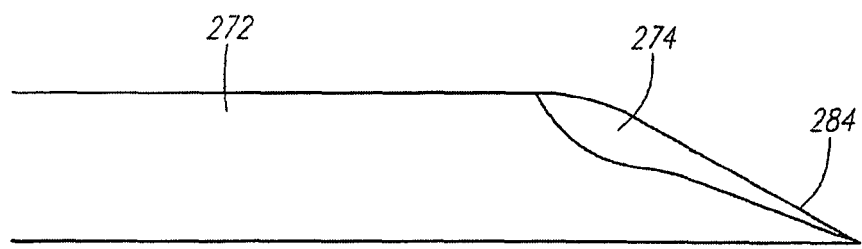
Figure 23C:
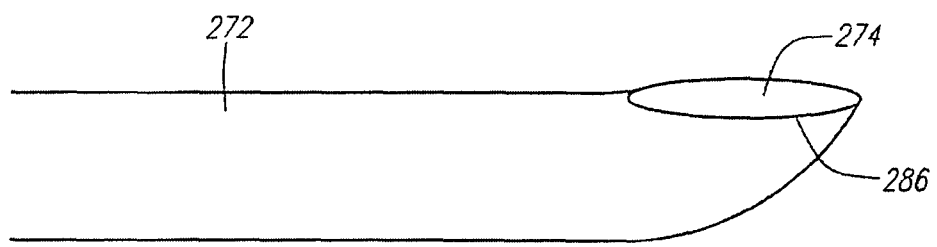

FIGS. 23A-C are side views of three embodiments of a needle body portion of a needle deployment assembly.

Figure 24A:
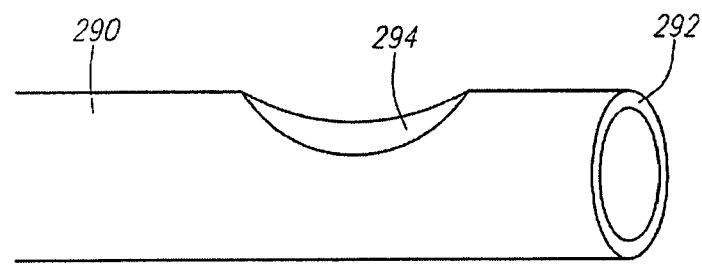

FIG. 24A is a side view of a tube having a side exit port.

Figure 24B:
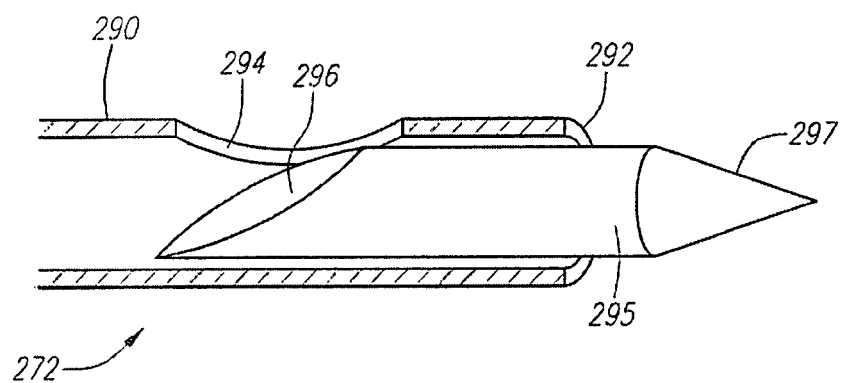

FIG. 24B is a side view of a needle body constructed using the tube of FIG. 24B.

Figure 25A:
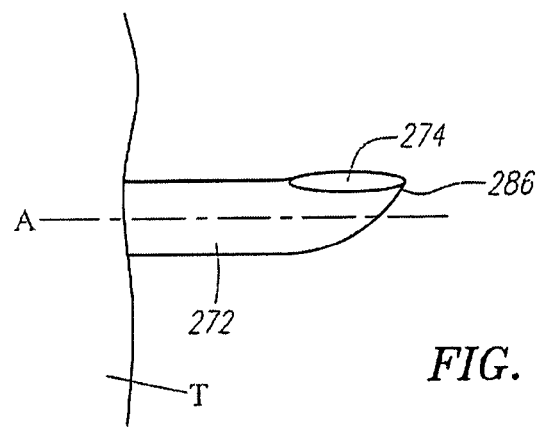
Figure 25B:
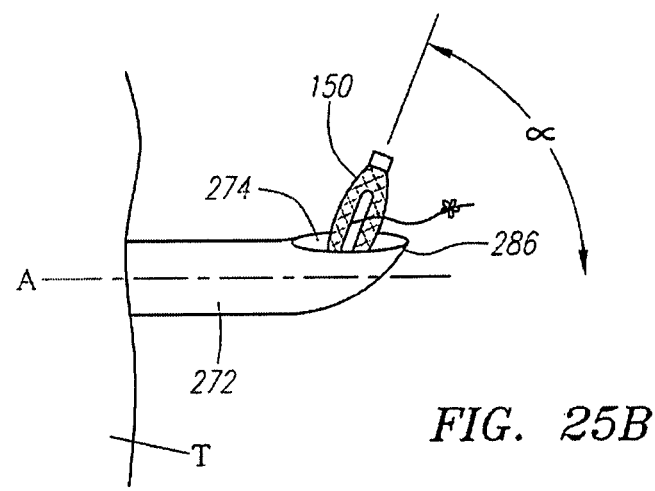
Figure 25C:
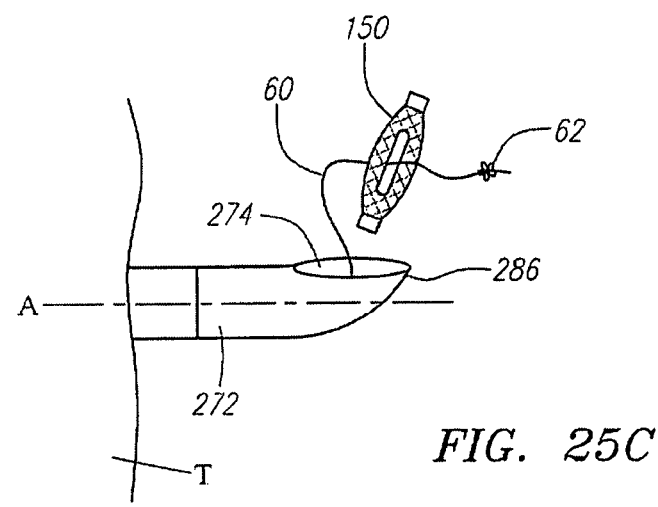

FIGS. 25A-C illustrate deployment of a tissue anchor from a needle body having an end configuration with a deflected point.

DETAILED DESCRIPTION

The devices described herein include several embodiments of tissue anchors, tissue anchor assemblies, and tissue anchor delivery systems. The methods described herein include several embodiments of methods for reconfiguring tissue, methods for joining portions of tissue together, and methods for deploying and using tissue anchors and tissue anchor systems.

The tissue anchors described herein are devices that have a contact surface adapted to engage an engagement surface of a portion of tissue and to coact with a connector, such as a suture, to maintain the tissue in a desired configuration or reconfiguration. In several of the embodiments described herein, the tissue anchors include a flat, large, or broad contact surface. In several of the embodiments, the tissue anchors have a first, low-profile shape and/or size to facilitate delivery, and a second, enlarged shape and/or size for deployment against a portion of tissue to be maintained in a desired configuration or reconfiguration. The tissue anchors are preferably formed of biocompatible and/or bioabsorbable materials.

The tissue anchor assemblies described herein include at least two tissue anchors that are attached to each other either directly or indirectly by a connector, such as a suture. The tissue anchor assemblies also include one or more retainer mechanisms, such as cinches, that perform the functions of retaining and/or adjusting the relative positions of the tissue anchors on the connector.

Several embodiments of tissue anchors and tissue anchor systems are described below in reference to the attached drawings. As noted above, one feature included in several of the tissue anchor embodiments described below is the provision of a substantially flat, large, or broad contact surface for engagement with the tissue when compared with conventional "T"-anchors, collared anchors, "T"-tags, staples, and other similar devices, or when compared with knots used during suturing procedures. The relatively flat, large, or broad contact surface is believed to provide several advantages over the conventional anchors and over conventional suturing procedures. For example, the large contact surface allows the anchor to rest substantially flat against the surface of the tissue so that the force imparted by the anchor is substantially evenly distributed over the engagement surface. This feature is believed to facilitate and promote tissue healing and reconfiguration. This feature is also believed, to increase the holding strength of the tissue anchor system, and increased the resistance to pull-through of the anchor (i.e., the tendency of an anchor to be pulled through a hole or other defect in the tissue under the tension force from the connector). Moreover, the absence of a collar or other component projecting from the contact surface of several of the tissue anchor embodiments described below allows the tissue anchor systems incorporating those anchors to more closely approximate portions of tissue, or to approximate portions of thin tissue more effectively than would otherwise be possible with conventional systems.

Figure 1A:
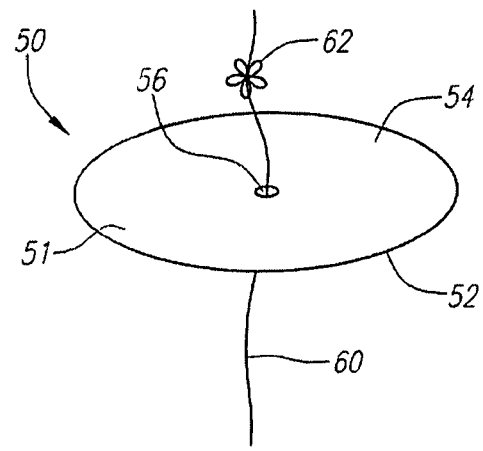
Figure 1B:
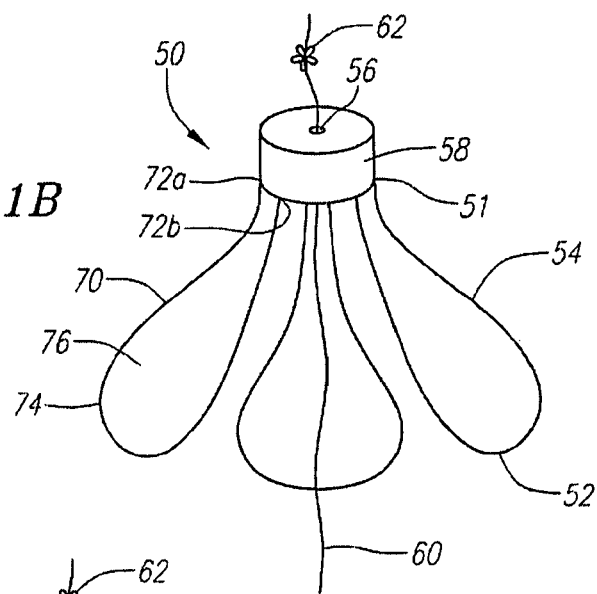
Figure 1C:
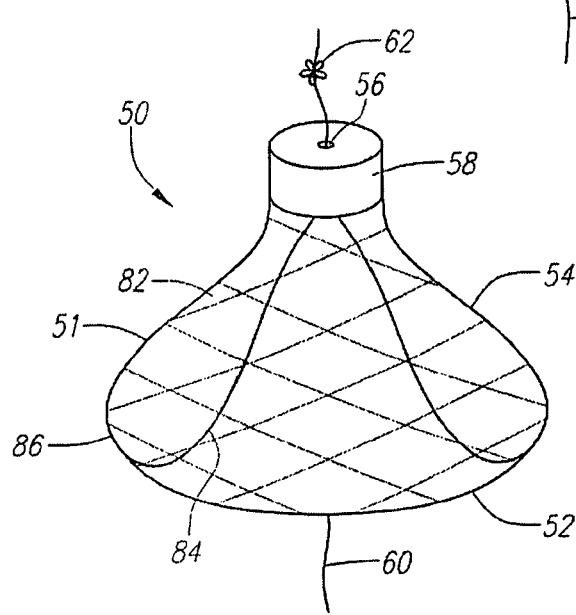

Turning first to FIGS. 1A-C, there are shown several embodiments of tissue anchors 50 suitable for use in the tissue anchor assemblies described herein. In each of the embodiments, the tissue anchor 50 includes a main body 51 having a broad contact surface 52 and an opposite, exposed surface 54. A passage 56 is provided to allow a connector, such as a suture 60, to pass through the anchor 50. A stop member, such as a knot 62 or a block, a bead or other member, is provided on the suture 60. The relative sizes of the knot 62 and the passage 56 are such that the knot 62 is unable to pass through the passage 56, thereby creating the ability for the suture 60 to apply a force to the tissue anchor 50 as the suture 60 is placed under tension.

Although a suture 60 is included in the embodiments illustrated in FIGS. 1A-C as well as several of the embodiments described below, alternative embodiments include connectors having other constructions and connectors formed of other materials. For example, in some embodiments, the connector is a wire, a fiber, a filament, a rod, or other member suitable for performing the functions of the connector.

In the embodiments shown and those described below, the main body 51 portion, the connector, the cinching mechanism, and the other components of the tissue anchor assembly are preferably formed of biocompatible and/or bioabsorbable materials, including but not limited to metals or metallic materials such as stainless steel, titanium, nickel, nickel-titanium alloy (i.e., Nitinol) or other alloys, plastics or other polymeric materials, biocompatible or bioabsorbable (e.g., PGA, PLA, PLG and other lactide-glycolide polymers and copolymers) suture, braid, or mesh, and other medical grade materials conventionally used for tissue anchors, sutures, implants, and similar devices. Several tissue anchor assembly embodiments are formed of combinations of these materials.

The main body 51 and the other components of the tissue anchor 50 are adapted to transition from a low-profile delivery configuration to be releasably received in a delivery device (such as a needle), and then to transition to a deployment configuration after delivery. In some embodiments, the transition to the deployment configuration is caused by spontaneous expansion due to the materials or construction of the tissue anchor 50. In other embodiments, the transition to the deployment configuration is caused or facilitated by retraction of the tissue anchor 50 against tissue.

In the embodiment shown in FIG. 1A, the main body 51 of the tissue anchor is a generally disk-shaped member. Although a circular disk is shown in the illustrated embodiment, other flat shapes (e.g., triangular, rectangular, irregular, etc.) are contemplated in alternative embodiments. The main body 51 is formed of a flexible material adapted to be rolled up or otherwise compressed into a low-profile delivery configuration to be releasably received in a delivery device (such as a needle), and then to transition to a deployment configuration (as shown in FIG. 1A) after delivery. In the deployment configuration, the contact surface 52 of the tissue anchor is able to be placed against the engagement surface of the tissue. As a tension force is applied to the suture 60, the knot 62 engages the exposed surface 54 of the main body 51, biasing it against the tissue.

In the embodiment shown in FIG. 1B, the main body 51 includes a plurality of loops 70 that are each attached to and that radiate from a central collar 58. At least two loops 70 are included, and the upper number of loops is limited only by the size of the loops in relation to the overall tissue anchor. The collar 58 is formed of a relatively rigid biocompatible or bioabsorbable material such as those described above. Each of the loops 70 is a wire of a resilient metal, plastic, or other material. Each loop 70 has two terminal ends 72a, 72b and an enlarged loop end 74 opposite the two terminal ends 72a, 72b. Each of the two terminal ends 72a, 72b is attached near to the other at the collar 58. The loop end 74 extends away from the collar 58 and defines a void space 76 within the loop. Due to its shape and materials, each loop 70 is fairly compressible, such that the loops 70 are able to be compressed into a delivery configuration and then expanded to a deployment configuration.

In the embodiment shown in FIG. 1C, the main body 51 is a generally cone-shaped member formed of a mesh or braid material. As described more fully below in relation to FIGS. 9A-C, the main body includes in a continuous mesh layer having an upper surface 82 and a lower surface 84, corresponding to the exposed surface 54 and the contact surface 52 of the anchor, respectively. The edges of the mesh layer are joined to the collar 58. In an alternative embodiment, the collar 58 is formed by heat fusing the edges of the mesh layer. The transition line 86 defined between the upper surface 82 and lower surface 84 defines the border of the main body 51. Due to its shape and the nature of the mesh material, the main body 51 is fairly compressible such that it is able to be compressed into a delivery configuration and then expanded to a deployment configuration.

Figure 2A:
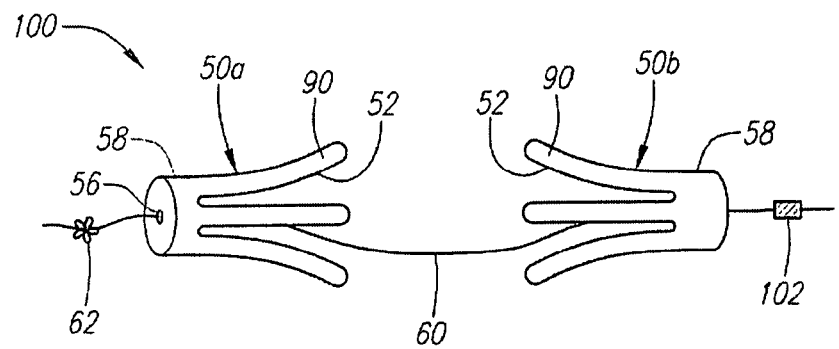
Figure 2B:
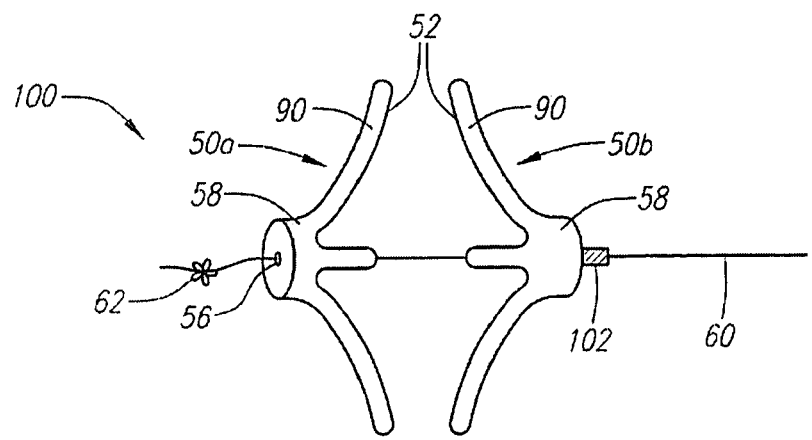

A tissue anchor assembly 100 is shown in FIGS. 2A-B. The tissue anchor assembly 100 includes a pair of tissue anchors including a distal anchor 50a and a proximal anchor 50b, each slidably attached to a connector (e.g., a suture 60). A cinching mechanism, such as a cinch 102, is provided on the suture 60. Additional information concerning the cinching mechanism is described below in relation to FIGS. 20A-B. In the embodiment shown, the anchors 50 each include a plurality of resilient struts 90 extending from and formed integrally with a central collar 58. In an alternative embodiment, the struts 90 are attached to but not integrally formed with the collar 58. The materials and construction of the anchors 50 are described more fully below in relation to FIGS. 3A-C.

FIG. 2A shows the tissue anchor assembly as it would appear in a transition state between delivery and complete deployment. Each of the anchors 50 is slidably attached to the suture 60 at a distance from one another, and the struts 90 are oriented generally in line with the longitudinal axis of the anchor 50. In FIG. 2B, the anchors 50 have been moved into close proximity to one another, and the struts 90 have been biased radially outward, away from the longitudinal axes of the anchors 50. The cinch 102 has been advanced to apply a force biasing the proximal anchor 50b toward the distal anchor 50a. This orientation is consistent with full deployment of the tissue anchor assembly, such as when a fold of tissue or one or more portions of tissue are interposed between the anchors 50. For clarity, no tissue is shown in FIGS. 2A-B.

The radial extension of the struts 90 of the anchors 50 creates an enlarged contact surface 52 for each of the anchors 50. As described above, the enlarged contact surface 52 provides advantages in applied forces, force distribution, and promotion of healing. In particular, because there is no collar 58 or other similar structure that forms or that is included on the contact surface 52 of the anchors, the contact surfaces 52 of the anchors 50 are able to come into close proximity to one another to more effectively approximate tissue interposed between the anchors.

In FIGS. 3A-D, there is shown a method for manufacturing the tissue anchor 50 described above in relation to FIGS. 2A-B. In FIG. 3A, a tube 92 of Nitinol (nickel-titanium alloy) or other suitable material is provided. The height and inner and outer diameters of the tube 92 are selected to provide desired dimensions of the tissue anchor 50 to be constructed. A plurality of longitudinal slits 94 are cut (e.g., by laser or other suitable cutting device) on the tube. (See FIG. 3B). The slits 94 extend from the bottom end of the tube 92 but do not extend over the entire length, ending at a position that will constitute the bottom end of the collar 58 of the completed anchor 50. After the slits 94 have been cut, the struts 90 formed thereby are flared radially outward, as shown in FIG. 3C. If the anchor material is Nitinol or other shape memory material, the anchor may be heat-set such that the struts 90 flare radially outward upon activation. Otherwise, the elastic properties of the material may be used to create the flared orientation for the struts 90.

In some embodiments, cut-in features are formed on portions of one or more of the struts 90. For example, in FIG. 3D, atraumatic end features 96 are formed on the bottom ends of each of the struts 90. The atraumatic end features 96 are broad, flattened portions at the terminal ends of the struts 90. The broad surfaces reduce the possibility of injury to the tissue. In some embodiments, a protective coating or covering is added to the atraumatic end feature to further enhance the level of protection provided.

FIGS. 4A-B and 5A-B show additional features that are optionally applied to the tissue anchors 50 described above. FIGS. 4A-B and 5A-B show top views and side views, respectively, of tissue anchors 50 formed generally in the manner described above in relation to FIGS. 3A-C. In the embodiment shown in FIGS. 4A-B, the struts 90 are each curled within a vertical plane to form a vertically curled terminal end 98. In the embodiment shown in FIGS. 5A-B, the struts 90 are each curled within a generally horizontal plane to form a horizontally curled terminal end 99. The vertically curled and horizontally curled terminal end features provide variations to the size of the contact surface 52 and to the resiliency of the struts 90 incorporated into the tissue anchors.

FIGS. 6A-C illustrate another embodiment of a method for forming a tissue anchor. Similar to the method described above, a tube of Nitinol or other suitable material is cut to form longitudinal slits 94 which define a plurality of struts 90. In addition, a second plurality of shorter slits 95 is formed between the longitudinal slits 94. The shorter slits do not extend to the bottom end of the tube 92. Instead, the shorter slits 95 are shorter than the lengths of the longitudinal slits 94. After the individual struts 90 are flared radially outward, the shorter slits 95 are expanded to define a void space or pocket 97 in each of the struts 90. The shorter slits may be expanded using, for example, a rod or other structure that is extended through the shorter slit 95 to pry the two sides apart. For those embodiments using Nitinol (or other shape memory material), after the struts 90 are flared radially and the pockets 97 are formed in each of the struts 90, the anchor 50 is heat set in its deployment configuration. The presence of the pockets 97 in each of the struts 90 creates a relatively larger engagement surface or "footprint" for each of the struts to contact the surface of the tissue.

FIGS. 7A-B each show an embodiment of a modified "basket" type anchor formed in a manner similar to the embodiments described above in relation to FIGS. 3A-C and 6A-C. A conventional "basket" anchor has a structure that includes a pair of collars that move toward one another to cause a collapsible "basket" portion extending between the two collars to expand radially. As the two collars move away from one another, the basket portion collapses radially inward. In contrast, the modified anchors described herein have a flat orientation in which the connector extends through the center of the anchor. Turning first to FIG. 7A, the anchor 50 includes an upper collar 110, a lower collar 112, a center strut 114, and a pair of side struts 116. A passage 56, through which a connector (e.g., a suture 60) is allowed to pass, is formed generally near the center of the center strut 114. In the embodiment shown, the components are formed from a tube of material (e.g., Nitinol). In other embodiments, the components are formed from a sheet of material. The side struts 116 each include an elbow portion 117 that extends radially away from the center strut 114. In the embodiment shown, each of the center strut 114 and the two side struts 116 are generally located in a single plane. The resultant anchor 50 thereby defines a generally flat, broad contact surface 52 for engagement with a portion of tissue.

In the embodiment shown in FIG. 7B, the center strut 114 is attached to the upper collar 110 but is not directly attached to the lower collar 112. Accordingly, the center strut 114 forms a cantilever in relation to the upper collar 110.

As noted above, several embodiments of tissue anchors described herein are formed of or incorporate woven materials, such as braid and/or mesh materials. As used herein, the term "mesh" refers to any of a variety of medical grade flexible woven fabric materials used in surgical and other medical applications. Conventional mesh materials are formed of polymeric (e.g., polyester, nylon, etc.) or metallic (e.g., stainless steel) materials. In several embodiments, the mesh is formed of bioabsorbable materials (e.g., PGA, PLA, PLG, or other lactide-glycolide polymers or copolymers).

Turning next to FIGS. 8A-B, a mesh sleeve 120 has a generally tubular shape. In some embodiments, the structure of the braids making up the mesh creates a disposition for the mesh sleeve to naturally collapse or draw down radially inward toward the longitudinal axis of the sleeve 120. This effect facilitates collapse of an anchor formed of mesh into a low-profile delivery configuration, followed by expansion of the mesh into a deployment configuration.

In addition, as shown in FIG. 8B, in some embodiments, the mesh material is capable of being fused by heating or other treatment. In the embodiment shown, a fused end 122 is formed at one end of the sleeve. The opposite end 124 remains open, thereby defining a contact surface 52 of the anchor 50. The flexibility of the mesh material allows the open end 124 to expand radially, providing a broad, flat contact surface when the anchor 50 is incorporated into a tissue anchor assembly 100.

Turning next to FIGS. 9A-C, a mesh sleeve 120 includes a first end 130 and a second end 132. The sleeve is inverted, and the second end 132 is fed back through the sleeve until it is located radially inward of the first end 130. (See FIG. 9B). The first end 130 and second end 132 are then heat fused to form a fused end 122 defining a passage 56 therethrough, thereby forming a tissue anchor 50. Relative to the embodiment described above in relation to FIGS. 8A-B, the tissue anchor 50 embodiment includes a transition line 86 that is non-fraying because it is formed of a continuous layer of mesh that has been doubled over.

Figure 10A:
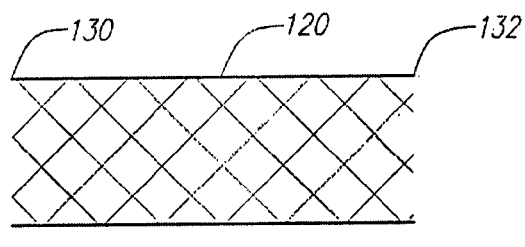
Figure 10B:
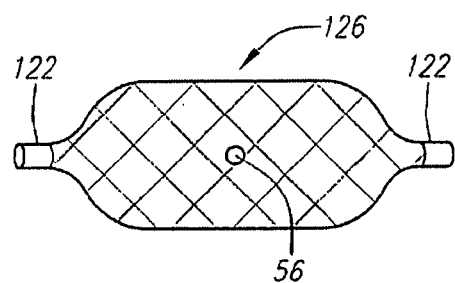

In FIGS. 10A-B, a mesh sleeve 120 is heat fused at both ends 130, 132 to form a mesh pouch 126 having a fused end 122 at both ends. A passage 56 is formed at or near the centroid of the mesh pouch 126. In the embodiment shown, the passage 56 is formed by heat fusing of the layers of mesh material. In other embodiments, an eyelet, a washer, or other similar object is placed within the pouch to define the passage 56.

Figure 11A:
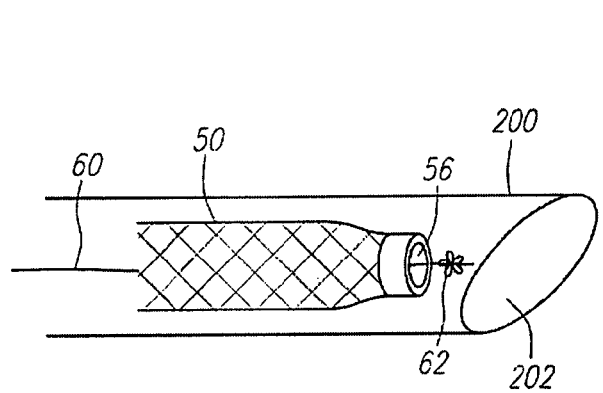
FIG. 11A is a schematic illustration showing an open-ended mesh anchor retained in its delivery configuration within a needle of a delivery device.
Figure 11B:
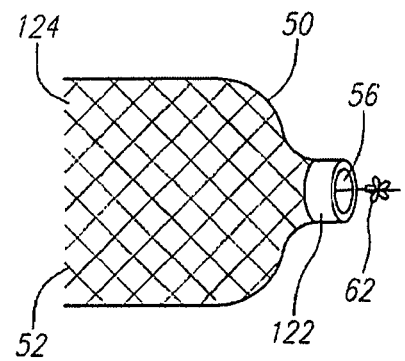
FIG. 11B is a side view of the mesh anchor of FIG. 11A shown after deployment.

FIGS. 11A-B and 12A-B illustrate deployment of two of the types of tissue anchors 50 described herein. Turning first to FIGS. 11A-B, a mesh umbrella-type tissue anchor 50 is shown in a delivery configuration inside a needle 200 of a delivery device. (See FIG. 11A). The needle 200 includes a sharp, beveled tip 202 adapted to penetrate tissue. The mesh tissue anchor 50 is collapsed and compressed to be received within the channel of the needle 200. Upon expulsion from the needle 200, the mesh tissue anchor 50 expands into a deployment configuration in which the open end 124 of the mesh expands radially outward to form a contact surface 52. (See FIG. 11B).

Figure 12A:
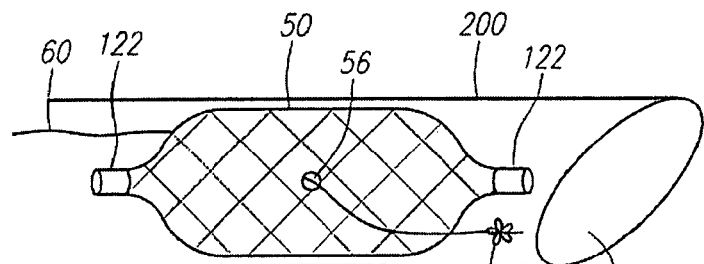
FIG. 12A is a schematic illustration showing a mesh pouch tissue anchor retained in its delivery configuration within a needle of a delivery device.
Figure 12B:
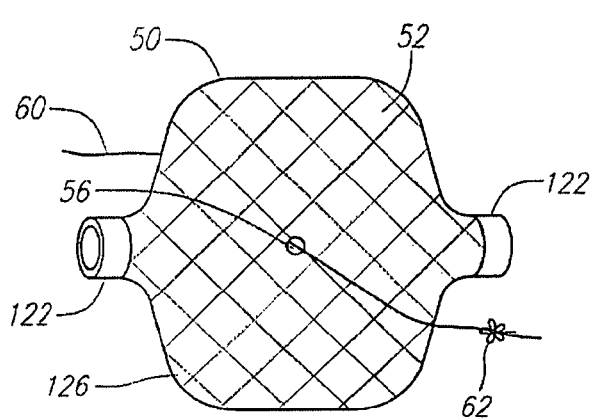
FIG. 12B is a side view of the mesh pouch tissue anchor of FIG. 12A shown after deployment.

In FIGS. 12A-B, a pouch-type mesh anchor 50 is shown in its low-profile delivery configuration (FIG. 12A) and its expanded deployment configuration (FIG. 12B). The pouch 126 is oriented laterally, rather than longitudinally, by the provision of the passage 56 at or near the centroid of the pouch. This orientation provides a large, broad, and flat contact surface 52 for exposure and engagement to the surface of the tissue.

In several embodiments of tissue anchors and tissue anchor assemblies described herein, the tissue anchor includes two or more components that are combined to form a composite tissue anchor. For example, in several embodiments, a mesh pouch or mesh umbrella structure is combined with a "T"-bar or strutted anchor. In those embodiments, the mesh pouch or umbrella is formed over the exterior of the T-bar or strutted anchor, whereby the T-bar or strutted anchor forms a skeletal structure that supports the mesh.

Turning to FIG. 13, a composite tissue anchor 150 includes a mesh umbrella 128 (such as those described above in relation to FIGS. 8B, 9C, and 11B) is laid over or attached to the upper surfaces of a strutted anchor 50 (such as those described above in relation to any of FIGS. 3C-D, 4A-B, 5A-B, and/or 6C). The strutted anchor 50 thereby provides additional support to the mesh umbrella 128. The mesh 128, in turn, provides additional surface contact with the engagement surface of the tissue, and facilitates healing by providing for additional tissue ingrowth.

In FIG. 14, a composite tissue anchor 150 includes a "T"-bar 140 that is retained within the interior of a mesh pouch 126. In the embodiment shown, the T-bar 140 is retained within the pouch 126, but is not attached directly to the pouch, i.e., it is allowed to "float" within the pouch. In other embodiments, the T-bar 140 is attached (e.g., by adhesive, by heat fusing, etc.) to the pouch 126 to be held in a fixed location within the pouch. The T-bar 140 is formed of a rigid material such as titanium, stainless steel, or other suitable metallic or polymeric material. The size and shape of the T-bar 140 is such that the T-bar 140 is able to be retained within the interior of the pouch 126. In the embodiment shown in FIG. 14, the T-bar 140 is substantially rectangular, having a passage 56 formed near its centroid. Other shapes are contemplated in alternative embodiments.

In FIGS. 15A-B, a composite tissue anchor 150 includes a central collar 142 that is applied over or incorporated onto or within a mesh pouch 126. In the embodiment shown, the central collar 142 is located at the approximate midpoint between the two fused ends 122 of the pouch 126, thereby forming a sub-pouch 127 on each side of the collar 142. The central collar 142 is formed of a rigid material and defines a passage 56 therethrough.

In the embodiment shown in FIG. 15B, the composite tissue anchor 150 includes a coil support structure 144 located within each of the sub-pouches 127. Each coil support structure 144 comprises a coil of Nitinol wire or other resilient material that is attached at a first end to a fused end 122 of the pouch and at a second end to the respective side of the central collar 142. The coil support 144 is adapted to be compressed when the composite tissue anchor 150 is in its delivery state, and to expand after the composite tissue anchor 150 has been deployed. A pair of coil supports 144 are included in the embodiment shown in FIG. 15B. In other embodiments, as few as one coil support 144 and as many as three or more coil supports 144 are included in the composite tissue anchor 150.

Turning next to FIG. 16, a composite tissue anchor 150 includes a mesh pouch 126 having a pair of fused ends 122 at opposite ends thereof. A passage 56 is formed at or near the centroid of the pouch 126. A support ring 146 is located within the interior of the mesh pouch 126. In the embodiment shown, the support ring 146 is retained within the pouch 126, but is not attached directly to the pouch, i.e., it is allowed to "float" within the pouch. In other embodiments, the support ring 146 is attached (e.g., by adhesive, by heat fusing, etc.) to the pouch 126 to be held in a fixed location within the pouch. The support ring 146 is formed of a resilient material such as nickel titanium alloy (Nitinol), stainless steel, or other suitable metallic or polymeric material. The size and shape of the support ring 146 is such that the support ring 146 is able to be retained within the interior of the pouch 126. In the embodiment shown in FIG. 16, the support ring 146 is substantially circular, and the support ring 146 extends substantially to the outer edges of the pouch 126. Other shapes and sizes for the support ring 146 are contemplated in alternative embodiments.

The support ring 146 is adapted to be collapsed, compressed, or otherwise reduced in profile when the composite tissue anchor 150 is retained within a delivery device or otherwise placed in its delivery state. Upon release from the delivery device, the resilient support ring 146 expands to its deployment state (as shown in FIG. 16), thereby also expanding the pouch 126 into the expanded state. In the embodiment shown, the support ring 146 is a continuous ring of resilient material. The ring is formed by cutting, stamping, or milling a ring shape from a sheet of material. In alternative embodiments, the support ring 146 is formed of a wire or similar member that is formed into a ring shape and attached at its ends, such as by welding, wrapping, or by a suitable collar or other connector.

The support ring 146 provides a degree of shape and support to the composite tissue anchor 150. Accordingly, in some embodiments, a shape or contour is applied to the support ring 146. For example, in an embodiment, opposed sides of the support ring 146 are bent out of plane to create a generally concave "C" shape to the composite tissue anchor 150 when viewed in profile. In another embodiment, the support ring 146 is bent into an "S" shape in profile, to provide another variation in the contact surface shape and resiliency. Other shape variations are also contemplated.

Another embodiment of a composite tissue anchor 150 is shown in FIG. 17. The composite anchor 150 includes a frame 148 formed of a resilient material such as nickel-titanium alloy (Nitinol), stainless steel, or other suitable metallic or polymeric material. A mesh sheet 134 or a plurality of mesh sheets is attached to (e.g., by adhesive or heat sealing) and extends across the interior of the frame 148. A passage 56 is formed or located near the centroid of the frame 148. In the embodiment shown in FIG. 17, the frame 148 is generally circular. In other embodiments, the frame 148 has a triangular shape, a square shape, an irregular shape, or another geometric or non-geometric shape.

The frame 148, formed of a resilient material, is adapted to collapse or compress into a low-profile delivery state, such as when the tissue anchor 150 is received within a delivery device (such as a needle 200). Upon expulsion from the delivery device, the frame 148 expands to its deployment state (as shown in FIG. 17).

FIG. 18A shows an exploded view of the components making up another embodiment of a composite tissue anchor 150. FIG. 18B shows the consolidated structure. The composite tissue anchor 150 includes a mesh pouch 126, a support ring 146 retained within the mesh pouch, and a cross-bar 140 also retained within the mesh pouch 126. In the embodiment shown, the support ring 146 is formed of nickel-titanium alloy (Nitinol), stainless steel, or other resilient metallic or polymeric material. In the embodiment, the cross-bar 140 is formed of titanium, stainless steel, or other rigid metallic or polymeric material. A passage 56 is defined by the cross-bar 140 and has a size and shape to allow the connector, such as a suture 60, to pass therethrough.

The composite tissue anchor 150 shown in FIGS. 18A-B has a slightly concave shape. The concavity is provided by the shape of the support ring 146 and also by the shape of the mesh pouch 126. In an embodiment, the concavity of the composite tissue anchor 150 enhances the degree of contact that the contact surface 52 has with the engaged tissue.

FIGS. 19A-B illustrate the general operation and some of the features of the tissue anchor assemblies described herein. The distal anchor 50a and suture 60 of the tissue anchor assembly 100 are delivered through a portion of tissue T. Delivery devices and methods of delivery are described in more detail below in relation to FIGS. 21-25. After delivery through the tissue T, the proximal anchor 50b and distal anchor 50a are moved into close proximity to one another to retain the tissue fold F. The cinch 102 is advanced on the suture 60 to bias the proximal anchor 50b toward the proximal anchor 50a. The contact surfaces 52 of the respective anchors 50 engage the surfaces of the tissue fold F.

Although the schematic diagram in FIGS. 19A-B and the associated description refers to tissue anchors 50, the figures and descriptions also apply to the composite tissue anchors 150 and other tissue anchors described herein. In addition, in several embodiments of the tissue anchors 50/150 and tissue anchor assemblies 100 described herein, the tissue anchor 50/150 is subject to being applied against tissue in either its forward orientation (i.e., with the contact surface 52 engaged against the tissue T), or in a reverse orientation (i.e., with the exposed surface 54 engaged against the tissue T). For example, in several of these embodiments, each of the tissue anchors 50/150 described above is deployed in its reverse orientation. In several of these embodiments, the tissue anchor 50/150 in its reverse orientation is capable of performing its tissue anchoring function and is more easily deployed from certain delivery devices due to the shape and resiliency of the main body 51 portion of the anchor.

In addition, for tissue anchor assemblies 100 that incorporate two or more tissue anchors 50/150, several embodiments include tissue anchors of different types within a single tissue anchor assembly. For example, in an embodiment, a tissue anchor assembly 100 includes a first composite tissue anchor 150 such as that described in relation to FIGS. 18A-B above, and a second anchor that comprises a known basket-type anchor. In another embodiment, a tissue anchor assembly 100 includes a first composite tissue anchor 150 such as that described in relation to FIGS. 18A-B above, and a second tissue anchor 50 such as that described above in relation to FIG. 9C. All other combinations of anchor types within a tissue anchor assembly are contemplated, including combinations that include the anchors described herein, combinations that include known tissue anchors, and combinations that include anchors such as those described in U.S. patent application Ser. Nos. 10/612,170; 10/840,950; 10/840,951; 10/841,245; 10/841,411; 10/865,736; 11/036,866; 11/036,946; and 11/404,423, each of which is hereby incorporated by reference in its entirety (including all references cited therein) as if fully set forth herein.

In addition, the tissue anchor assembly shown in FIGS. 19A-B includes a single cinch 102 movably attached to the suture 60 at a point proximal to the proximal anchor 50b. In alternative embodiments, a distal cinch is provided on the suture 60 at a point distal of the distal anchor 50a, in place of (or in addition to) the stop member 62. In this alternative embodiment, the anchors 50a, 50b are able to be brought into proximity to one another and retained via advancement of either the first cinch 102, the distal cinch, or both cinches.

As noted above, a cinch 102 is a suitable member for use as the cinching mechanism included in the tissue anchor assemblies described herein. The cinch 102 functions by providing uni-directional translation over the suture, thereby providing the ability to advance the tissue anchor(s) 50/150 into apposition and to retain the anchor(s) in place. An embodiment of a cinch 102 is shown in FIGS. 20A-B. The cinch includes a generally tubular body 103 defining an internal lumen 104. A plurality of inwardly facing levers 105 are formed integrally with the side wall of the tubular body 103. Three levers 103 are included in the cinch embodiment shown in the figures. In other embodiments, fewer levers (e.g., one or two) or more than three levers are used. In some embodiments, each lever 105 is flexibly biased to spring radially inward into the tubular body 103 or to deflect radially outward upon a suture 60 or other connector member passing therethrough. During translation of the suture 60 in a first direction (i.e., from left to right as viewed in FIG. 20B), the suture 60 is allowed to freely pass through the tubular body and past the plurality of levers due to a slight radially outward pivot of each of the levers. However, when the suture is urged in the second direction (i.e., from right to left as viewed in FIG. 20B), the levers 105 pivot radially inward, cinching down upon the suture against the inner surface of the tubular body 103. The cinching levers 105 are configured to prevent or inhibit the overcinching or cutting of the suture 60.

In other embodiments of the cinch 102, the levers 105 are substantially rigid, and do not pivot or deflect. In those embodiments, the levers 105 create a sufficiently tortuous path for the suture 60 (or other connector) to traverse that the cinch effectively binds the suture from translating in the first direction, while allowing translation in the second direction.

The cinches 102 described herein are formed of biocompatible and/or bioabsorbable materials such as those described above. In several embodiments, the cinch is formed of nickel-titanium alloy (Nitinol). The size and shape of the cinch are primarily dependent upon the size and shape of the other parts of the tissue anchor assembly, such as the diameter and materials forming the suture 60 (or other connector) and/or the size of the passage 56 in the tissue anchors 50/150. Additional embodiments of cinches and additional cinching mechanisms suitable for use in the tissue anchor assemblies 100 are described and illustrated in U.S. patent application Ser. Nos. 10/612,170; 10/840,950; 10/840,951; 10/841,245; 10/841,411; 10/865,736; 11/036,866; 11/036,946; and 11/404,423, each of which is hereby incorporated by reference in its entirety (including all references cited therein) as if fully set forth herein.

The tissue anchor assemblies 100 described herein are suitable for use in surgical, diagnostic, and other therapeutic procedures that are performed endoscopically, laparoscopically, endoluminally, or in open procedures. In several embodiments, a suitable delivery device is used to deploy the tissue anchors 50/150 and tissue anchor assemblies 100 endoscopically and/or laparoscopically. An example of a suitable delivery device is shown in FIG. 21, and is described in more detail in U.S. patent application Ser. No. 11/070,846, which is hereby incorporated by reference in its entirety (including all references cited therein) as if fully set forth herein. The delivery device 208 is described briefly below.

In manipulating tissue or creating tissue folds, a device having a distal end effector may be advanced endoluminally, e.g., transorally, transgastrically, etc., into the patient's body, e.g., the stomach. The tissue may be engaged or grasped and the engaged tissue may be manipulated by a surgeon or practitioner from outside the patient's body. Examples of creating and forming tissue plications may be seen in further detail in U.S. patent application Ser. No. 10/955,245, filed Sep. 29, 2004, which is incorporated herein by reference, as well as U.S. patent application Ser. No. 10/735,030, filed Dec. 12, 2003, which is also incorporated herein by reference in its entirety.

In engaging, manipulating, and/or securing the tissue, various methods and devices may be implemented. For instance, tissue securement devices may be delivered and positioned via an endoscopic apparatus for contacting a tissue wall of the gastrointestinal lumen, creating one or more tissue folds, and deploying one or more tissue anchors through the tissue fold(s). The tissue anchor(s) may be disposed through the muscularis and/or serosa layers of the gastrointestinal lumen.

The delivery device 208 shown in FIG. 21 generally comprises a tissue manipulation assembly 210 and a needle deployment assembly 260. The tissue manipulation assembly 210 includes a flexible catheter or tubular body 212 which is configured to be sufficiently flexible for advancement into a body lumen, e.g., transorally, percutaneously, laparoscopically, etc. The tubular body 212 is configured to be torqueable through various methods, e.g., utilizing a braided tubular construction, such that when a handle 216 is manipulated and/or rotated by a practitioner from outside the patient's body, the longitudinal and/or torquing force is transmitted along the body 212 such that the distal end of the body 212 is advanced, withdrawn, or rotated in a corresponding manner.

A tissue manipulation end effector 214 is located at the distal end of the tubular body 212 and is generally used to contact and form tissue folds and/or to otherwise bring portions of tissue into apposition. The tissue manipulation end effector 214 is connected to the distal end of the tubular body 212 via a pivotable coupling 218. A lower jaw member 220 extends distally from the pivotable coupling 218 and an upper jaw member 222, in this example, is pivotably coupled to the lower jaw member 220 via a jaw pivot 226. The location of the jaw pivot 226 may be positioned at various locations along the lower jaw 220 depending upon a number of factors, e.g., the desired size of the "bite" or opening for accepting tissue between the jaw members, the amount of closing force between the jaw members, etc. One or both jaw members 220, 222 may also have a number of protrusions, projections, grasping teeth, textured surfaces, etc. on the surface or surfaces of the jaw members 220, 222 facing one another to facilitate the adherence of tissue between the jaw members 220, 222.

A launch tube 228 extends from the handle 216, through the tubular body 212, and distally from the end of the tubular body 212 where a distal end of the launch tube 228 is pivotally connected to the upper jaw member 222 at a launch tube pivot 230. A distal portion of the launch tube 228 may be pivoted into position within a channel or groove defined in upper jaw member 222, to facilitate a low-profile configuration of tissue manipulation end effector 214. When articulated, either via the launch tube 228 or other mechanism, the jaw members 220, 222 may be urged into an open configuration to receive tissue in the opening between the jaw members 220, 222.

The launch tube 228 may be advanced from its proximal end at the handle 216 such that the portion of the launch tube 228 that extends distally from the body 212 is forced to rotate at a hinge or pivot 230 and reconfigure itself such that the exposed portion forms a curved or arcuate shape that positions the launch tube opening perpendicularly relative to the upper jaw member 222. The launch tube 228, or at least the exposed portion of the launch tube 228, may be fabricated from a highly flexible material or it may be fabricated, e.g., from Nitinol tubing material which is adapted to flex, e.g., via circumferential slots, to permit bending.

Once the tissue has been engaged between the jaw members 220, 222, a needle deployment assembly 260 is urged through the handle 216, though the tubular body 212, and out through the launch tube 228. The needle deployment assembly 260 may pass through the lower jaw member 220 via a needle assembly opening (not shown in the drawing) defined in the lower jaw member 220 to pierce through the grasped tissue. Once the needle deployment assembly has been passed through the engaged tissue, one or more tissue anchors of a tissue anchor assembly 100 (see FIG. 22) are deployed for securing the tissue, as described in further detail herein and in U.S. patent application Ser. No. 10/955, 245, which has been incorporated by reference above.

FIG. 22 shows additional details relating to the needle deployment assembly 260. As mentioned above, a needle deployment assembly 260 may be deployed through the tissue manipulation assembly 210 by introducing needle deployment assembly 260 into the handle 216 and through the tubular body 212, as shown in the assembly view of FIG. 21, such that the needle assembly 266 is advanced from the launch tube and into or through approximated tissue. Once the needle assembly 266 has been advanced through the tissue, the anchor assembly 100 may be deployed or ejected. The anchor assembly 100 is normally positioned within the distal portion of a tubular sheath 264 that extends from a needle assembly control or housing 262. Once the anchor assembly 100 has been fully deployed from the sheath 264, the spent needle deployment assembly 260 may be removed from the tissue manipulation assembly 210 and another needle deployment assembly may be introduced without having to remove the tissue manipulation assembly 210 from the patient. The length of the sheath 264 is such that it may be passed entirely through the length of the tubular body 212 to enable the deployment of the needle assembly 266 into and/or through the tissue.

The elongate and flexible sheath or catheter 264 extends removably from the needle assembly control or housing 262. The sheath or catheter 264 and the housing 262 may be interconnected via an interlock 270 which may be adapted to allow for the securement as well as the rapid release of the sheath 264 from the housing 262 through any number of fastening methods, e.g., threaded connection, press-fit, releasable pin, etc. The needle body 272, which may be configured into any one of the variations described above, extends from the distal end of the sheath 264 while maintaining communication between the lumen of the sheath 264 and the needle opening 274.

An elongate pusher 276 comprises a flexible wire or hypotube that is translationally disposed within the sheath 264 and movably connected within the housing 262. A proximally-located actuation member 278 is rotatably or otherwise connected to the housing 262 to selectively actuate the translational movement of the elongate pusher 276 relative to the sheath 264 for deploying the anchors from the needle opening 274. The tissue anchor assembly 100 is positioned distally of the elongate pusher 276 within the sheath 264 for deployment from the sheath 264. Needle assembly guides 280 protrude from the housing 262 for guidance through the locking mechanism described above.

Several embodiments of the needle body 272 and the orientation of the needle opening 274 are shown in FIGS. 23A-C. In the embodiment shown in FIG. 23A, the needle body 272 includes an end configuration that incorporates an edge having a single grind or cut point 282. In the embodiment shown in FIG. 23B, the end configuration incorporates a multi-faceted edge 284. In the embodiment shown in FIG. 23C, the end configuration incorporates a deflected point 286, such as a Tuohy needle. These embodiments are exemplary, and are not intended to be limiting. Other needle body variations are also contemplated to obtain desired results.

For example, in FIGS. 24A-B, another embodiment for the needle body 272 includes a tube 290 having a blunt distal end 292 and a side exit port 294 formed through the side wall at a short distance from the distal end 292. An insert 295 is located within the distal portion of the tube 290. The insert 295 includes an inclined surface 296 facing proximally within the tube 290 and aligned with the side exit port 294, and a piercing surface 297 formed on the distal end, extending longitudinally from the distal end of the tube 290. The inclined surface 296 and exit port 294 operate to provide a ramp and exit port for deployment of a tissue anchor or tissue anchor assembly via a side port exit, rather than a straight, distal port exit. Although described and illustrated as separate structures, the tube 290 and insert 295 may also be formed as a single structure.

When a tissue anchor 50/150 is deployed from a delivery device having a needle deployment assembly 260, a side-oriented exit port from the needle body 272 may facilitate a preferred orientation of the anchor 50/150 relative to the tissue. For example, as shown in FIGS. 25A-C, after expulsion from the needle body 272, a flat tissue anchor 150 must toggle relative to the suture 60 in order to be properly oriented relative to the surface of the tissue T. If the anchor 150 does not toggle, and instead remains generally aligned with the suture 60, the possibility is increased that the anchor 150 will pull through the channel in the tissue T created by the needle body 272 as the needle is refracted after delivery of the anchor 150. In the embodiment shown, the needle body 272 includes an end configuration that includes a deflected point 286. As a result, the needle opening 274 is oriented at an angle α relative to the longitudinal axis A of the needle body 272. Accordingly, as the tissue anchor 150 is deployed, the longitudinal axis of the tissue anchor 150 is effectively "pre-toggled," i.e., shifted from its alignment with the needle tract, thereby reducing the likelihood of pull through. A similar result is obtained using the needle body structure described above in relation to FIGS. 24A-B.

As discussed above, the tissue anchors, tissue anchor assemblies, and delivery devices described herein are suitable for use in a variety of surgical, diagnostic, and/or therapeutic procedures in which one or more portions of tissue are to be approximated, brought into apposition, joined, manipulated, or otherwise reconfigured. The devices and methods are particularly suitable for translumenal procedures (e.g., transoral, gastric, or gastroesophageal procedures; transrectal or colonic procedures; transvaginal procedures; natural orifice translumenal endoscopic surgical or "NOTES" procedures; and others). Several translumenal procedures are described in U.S. patent application Ser. No. 10/841,233, Ser. No. 10/898,683, Ser. No. 11/238,279, Ser. No. 11/102,571, Ser. No. 11/342,288, and Ser. No. 11/270,195, which are hereby incorporated by reference. The medical instruments described herein are suitable for use in combination with, for example, the endoluminal tool deployment systems described in U.S. patent application Ser. No. 10/797,485 and Ser. No. 11/738,297, which are hereby incorporated by reference. In particular, the tool deployment systems described in the '485 application and the '297 application include one or more lumens suitable for facilitating deployment of the medical instruments described herein to perform or assist in performing endoscopic, laparoscopic, or NOTES diagnostic or therapeutic procedures.

Although various illustrative embodiments are described above, it will be evident to one skilled in the art that various changes and modifications are within the scope of the invention. It is intended in the appended claims to cover all such changes and modifications that fall within the true spirit and scope of the invention.

The invention claimed is:

1. A surgical tissue anchor assembly, comprising:
   a first tissue anchor, a second tissue anchor, and a connector;
   the first and second tissue anchors each including:
      a first collar at a first end of a flexible mesh pouch;
      a second collar at a second end of the flexible mesh pouch, and the connector passing through the flexible mesh pouch and not through the first and second collars of the first and second tissue anchors;

a frame within the flexible mesh pouch, with the frame having longitudinal resilient struts flared radially outwardly, with the first and second tissue anchors each reconfigurable from a low profile delivery configuration to an expanded deployed position, via outward movement of the resilient struts; and a stop member on the connector not passable through the first tissue anchor.

2. The surgical tissue anchor assembly of claim 1 with the connector passing through a central area of the mesh pouch of the first and second tissue anchors.

3. The surgical tissue anchor assembly of claim 2 with each tissue anchor further including a bar within the mesh, with the connector passing through the bar.

4. The surgical tissue anchor assembly of claim 1 with the frame retained within the flexible mesh pouch, but not attached to the flexible mesh pouch.

5. The surgical tissue anchor assembly of claim 1 with the first and second tissue anchors slidable along the connector, and wherein the connector comprises suture.

6. The surgical tissue anchor assembly of claim 1 with the frame comprising a tube having longitudinal slits between the struts.

7. The surgical tissue anchor assembly of claim 1 wherein the tissue anchors are flat.

8. A surgical tissue anchor assembly, comprising:
a first tissue anchor, a second tissue anchor, and a connector;
the first and second tissue anchors each including:
flexible mesh pouch;
a frame retained within the flexible mesh pouch, but not attached to the flexible mesh pouch,
the frame comprising longitudinal struts resiliently biased radially outwardly;
with the first and second tissue anchors each reconfigurable from a low profile delivery configuration to an expanded deployed position, via the resilient bias of the struts;
the connector passing through the flexible mesh pouch of each of the first and second tissue anchors, and through a bar retained within the flexible mesh pouch of each of the first and second tissue anchors; with the first and second tissue anchors slidable along the connector; and a stop member on the connector, with the stop member not passable through the first tissue anchor.

9. The surgical tissue anchor assembly of claim 8 with the bar in each tissue anchor not attached to the flexible mesh pouch.

10. The surgical tissue anchor assembly of claim 9 with the connector comprising absorbable suture and with the first and second tissue anchors slidable along the suture.

11. The surgical tissue anchor assembly of claim 10 with the pouch comprising a tubular mesh sleeve having closed ends, and with the suture not extending through the closed ends.

12. The surgical tissue anchor assembly of claim 11 wherein each closed end has a flat end surface and a cylindrical side wall.

13. The surgical tissue anchor assembly of claim 8 with the connector comprising a suture passing through a central section of the mesh pouch of each of the first and second tissue anchors.

14. The surgical tissue anchor assembly of claim 13 wherein the suture passes through a central opening of the bar.

15. A surgical tissue anchor comprising:
a mesh pouch;
a frame within the mesh pouch, with the frame having longitudinal resilient struts projecting radially outwardly, with the resilient struts holding the mesh pouch in an expanded position, and with the mesh pouch contractable into a low profile delivery position;
a bar retained within the mesh pouch and not attached to the mesh pouch;
a suture passing through a central area of the mesh pouch and through an opening at a central area of the bar.

16. The surgical tissue anchor of claim 15 with the mesh pouch comprising a tubular mesh sleeve having first and second fused ends.

17. The surgical tissue anchor of claim 15 wherein the mesh pouch is flat when in the expanded position.

18. The surgical tissue anchor of claim 15 wherein the bar is rigid and the pouch is flexible.

19. The surgical tissue anchor of claim 15 wherein the suture is bioabsorbable.

* * * * *